United States Patent [19]
Huang et al.

[11] 3,987,064
[45] Oct. 19, 1976

[54] METHOD FOR PRODUCING CITRACONIC ANHYDRIDE

[75] Inventors: I-Der Huang, West Paterson; Martin B. Sherwin, Wayne; Andrew Westner, Paramus, all of N.J.

[73] Assignee: Pfizer Inc., New York, N.Y.

[22] Filed: June 3, 1975

[21] Appl. No.: 583,510

[52] U.S. Cl.......................................... 260/346.8 A
[51] Int. Cl.². ..................................... C07D 307/60
[58] Field of Search ................................ 260/346.8

[56] References Cited
UNITED STATES PATENTS
3,503,999  3/1970  Pichler et al..................... 260/346.8
FOREIGN PATENTS OR APPLICATIONS
1,157,117  7/1969  United Kingdom............... 260/346.8

OTHER PUBLICATIONS

Nagamawari et al., Chem. Abst., vol. 61, Col. 578–579 (1964).

Miyamori et al., Chem. Abst., vol. 78, item 15536 (1973).

Kawai et al., Chem. Abst., vol. 80, item 70353 (1974).

Shirai et al., Chem. Abst., vol. 75, item 129649 (1971).

*Primary Examiner*—Henry R. Jiles
*Assistant Examiner*—Bernard Dentz
*Attorney, Agent, or Firm*—Connolly and Hutz

[57] ABSTRACT

Described is a method for producing citraconic anhydride by vapor phase oxidation of isoamylene or isoprene in the presence of a catalyst consisting essentially of antimony, molybdenum and oxygen in combined form. By using the catalyst disclosed with the hydrocarbons to be oxidized, high yields of citraconic anhydride containing a minimal amount of maleic anhydride are obtained.

8 Claims, No Drawings

METHOD FOR PRODUCING CITRACONIC ANHYDRIDE

BACKGROUND OF THE INVENTION

It is well known that various dicarboxylic acid anhydrides can be produced by vapor phase catalytic oxidation of various hydrocarbons. The existing literature and patent data indicate, however, that the production of appreciable amounts of citraconic anhydride by the catalytic oxidation of isoamylenes is rather difficult. This oxidation produces predominantly maleic anhydride and only relatively small amounts of citraconic anhydride with a large number of known oxidation catalysts. Belostotskaya et al [Neftekhimiya 8 (3), 379 (1968)] reported that citraconic acid was obtained with yields of not more than 3.3 percent from isoamylene oxidation over vanadium-based catalysts, while Butt et al [J. Catalysis 5, 205 (1966)] did not even find traces of citraconic anhydride in the oxidation products during their fundamental study of the oxidation of the three isoamylenes over a $V_2O_5$ catalyst system.

The main drawback in developing a catalytic oxidation process for producing citraconic anhydride in general is the lack of direct analogy between this oxidation process and the processes for oxidizing hydrocarbons to maleic anhydride. Maleic anhydride has been commercially prepared from a variety of hydrocarbon stocks such as benzene, butene and butane. However, the oxidation catalysts used in these preparations often cannot be applied to citraconic anhydride production. In oxidizing benzene over a vanadium-based catalyst, Halcon [German patent 1,173,891 (1964)] indicated an 80 percent yield to maleic anhydride. Using a similar catalyst, Pichler et al, in their extensive studies, were able to detect only trace quantities of citraconic anhydride in the oxidation products of toluene, m-xylene, p-xylene and cresol [Brennstoff-Chemie, 45, 97–103 (1964); 46, 258–64 (1965)]. Similarly, in the oxidation of butene over a vanadium/phosphorous-based catalyst, yield to maleic anhydride was reported to be 57.2 percent (U.S. Pat. No. 3,478,063) whereas in the oxidation of methylbutene using a similar vanadium/phosphorous-based catalyst, maximum yield to citraconic anhydride was only 1.9 percent [Neftekhimiya 8 (3), 379–85 (1968)].

It is therefore clear that catalysts which are active in oxidizing hydrocarbons to maleic anhydride are not necessarily effective in oxidizing the corresponding hydrocarbons containing one or more additional methyl groups to citraconic anhydride, although some of the patent literature limited to specific catalysts, for example, U.S. Pat. Nos. 3,221,049, 3,226,337 and 3,255,213, implies otherwise.

U.S. Pat. No. 3,094,539 describes the production of aliphatic dicarboxylic acid anhydrides, specifically maleic anhydrides, by vapor phase oxidation of ethylenically unsaturated aliphatic hydrocarbons of 4 to 6 carbon atoms, including isoprene and 3-methyl-1-butene, but preferably 4-carbon hydrocarbons, in the presence of catalysts, for example, a vanadium-molybdenum catalyst. The patent states that yields can be improved by the addition of antimony to the vanadium-containing catalyst. A similar catalyst for vapor phase oxidation of unsaturated aldehydes to $\alpha,\beta$-unsaturated carboxylic acids such as acrylic acid is described in U.S. Pat. No. 3,408,392, while a similar oxidation using an antimony-molybdenum-arsenic catalyst is described in U.S. Pat. No. 3,280,182.

Japanese Patent Sho 47-38425 of Sept. 28, 1972, describes vapor phase oxidation of isoprene in the presence of a vanadium oxide catalyst containing molybdenum oxide and/or arsenic oxide.

In Pitchler Dutch Patent 7,301,973, opened for inspection on Aug. 14, 1973, citraconic anhydride is produced by vapor phase oxidation of one or more alkyl-substituted monoalkenes, such as 2-methyl-2-butene and 3-methyl-1-butene, in contact with a catalyst comprising vanadium and at least one metal from Group Six of the Periodic System, such as chromium, molybdenum, tungsten or uranium, additionally optionally containing as a promoter one or more oxides of titanium, phosphorous, tin, aluminum or silicon.

British Patent 1,353,397, published May 15, 1974, discloses the production of maleic anhydride by the oxidation of paraffins having 4 or 5 carbon atoms, preferably butanes such as n-butane, in the presence of a catalyst having the formula $A_aB_bSb_cMo_dO_e$ wherein A is iron and/or vanadium, B is at least one of aluminum, chromium, cobalt, nickel, copper, bismuth, tellurium, boron, phosphorus and tungsten, $a$ is 0.1 to 6, $b$ is 0 to 3, $c$ is 0.1 to 12, $d$ is 12 to 0.1 and $e$ is a number determined by the valence requirements of the combined elements other than oxygen present in the catalyst.

BRIEF DESCRIPTION OF THE INVENTION

In accordance with the present invention, it has been found that a catalyst consisting essentially of an antimony-molybdenum-oxygen complex is highly effective in converting isoamylenes and isoprene predominantly to citraconic anhydride at yields as high as about 60 percent by weight or more per pass and with a molar selectivity as high as about 20 or more under the reaction conditions specified hereinafter. Although minor amounts of additional active catalytic elements may be present in the catalyst, it has been found that the catalyst should consist essentially of antimony, molybdenum and oxygen since other active catalytic elements previously suggested for vapor phase oxidation have proven detrimental to the yield and/or selectivity of the catalyst.

As used herein, "molar selectivity" means the moles of citraconic anhydride divided by the moles of maleic anhydride present in the oxidation product. The reaction yield for the preparation of citraconic anhydride is improved by decreasing the molybdenum content since catalysts having a high molybdenum content form relatively high contents of maleic anhydride. Nevertheless, citraconic anhydride is the major oxidation product even when the molybdenum content in the catalyst system is increased to nearly 100 percent.

DETAILED DESCRIPTION OF THE INVENTION

In preparing the active catalyst according to the present invention, the atomic ratio of antimony to molybdenum should be maintained in the broad range of from about 0.01 to 100, preferably from about 0.05 to 50 atoms of antimony per atom of molybdenum, and more preferably from about 0.05 to 15 atoms of antimony per atom of molybdenum. The amount of oxygen in the catalyst will vary depending upon the valence requirements of the antimony and molybdenum, and is not critical to the effectiveness of the catalyst.

The catalyst of this invention, as with catalysts of the prior art, can be satisfactorily employed either unsupported or supported. The catalyst can be supported on any suitable carrier such as zirconium oxide, silica, aluminum oxide, silicon carbide, titanium dioxide, diatomaceous earth and the like, or it may be simply coated on a metal or other solid material such as glass, ceramic, stainless steel, aluminum or silver. The solid supports may be in the form of balls, shavings, rings, saddles and the like. If a suitable support is employed, it is used in amounts ranging from about 10 to 98 weight percent of the total catalyst.

The catalyst according to the present invention may be prepared in a number of ways. A preferred method because of its simplicity is to prepare a complex in solution or slurry form and deposit the complex onto a suitable carrier. According to one preferred method, antimony oxide (e.g., $Sb_2O_3$, $Sb_2O_4$, $Sb_2O_5$) and molybdenum oxide (e.g., $MoO_3$, $MoO_2$, $Mo_2O_3$) are suspended in water and heated to boiling; the quantity of water used in the system is not critical. The slurry changes color during refluxing, indicating that an oxidation-reduction reaction has taken place between molybdenum and antimony to form the desired antimony-molybdenum-oxygen complex. Water is then removed by evaporation until a thick paste is obtained. The paste is then deposited onto a carrier, or diluent, and dried overnight, preferably at elevated temperature, for example, 100° C. or higher. The paste may of course be dried directly without using a carrier. The resultant product is ground and used in granular form or is pelletized to a defined geometric shape.

When a metal or other solid support is used, it is preferred to heat the support to an elevated temperature, for example, between about 150° and 250° C., and dip it into the antimony-molybdenum-oxygen paste. The coated supports are then dried in an oven at, for example, 200° C. The coating process can be repeated until the solid support is completely covered with the active catalyst.

Many other processes for preparing the catalyst according to this invention will be apparent to those skilled in the art. For example, instead of the oxides mentioned above, it is possible to utilize antimony and/or molybdenum precursors of the oxides which are converted to the oxide complex under the preparation conditions employed. The oxides of the invention or precursors thereof may also be coprecipitated from solution and then converted if necessary by heat to the desired complex.

The catalyst may be calcined if desired but calcination is not essential. When calcining the catalyst, it is preferred to operate below about 500° C. Heating the catalyst composition to convert precursors to the desired antimony-molybdenum-oxygen complex, such as by decomposition, may be desired depending upon the precise method chosen for producing the catalyst.

The catalyst may be placed directly in the reactor used to convert hydrocarbon to citraconic anhydride and may be used as is without conditioning. In a typical but not limiting example, the reactor temperature is rapidly raised to 400° to 450° C. Thereafter, the hydrocarbon in air, for example, is passed over the catalyst at a desired rate as specified hereinafter; oxidation product containing predominantly citraconic acid is collected from the start of the run.

The desired feedstock, preferably isoamylene, is fed to the catalytic reaction zone mixed with air or other molecular oxygen-containing gas such as oxygen in carbon dioxide, oxygen in steam and the like. The optimum mixture is dependent on whether fixed bed or fluid bed is used. The mole, or volume, percent isoamylene in the mixture ranges from about 0.1 to 4, preferably from about 0.4 to 1.6, for a fixed bed process, and from about 1 to 20, preferably from about 2 to 6, for a fluid bed process. The stoichiometric ratio of oxygen to isoamylene may generally range from about 1 to 250, preferably about 4 to 100. In selecting the concentrations of oxygen and isoamylene, due regard must be given to the explosive limits of the mixture.

Since the reaction of the present invention is highly exothermic, it is necessary in designing the reactor to give sufficient consideration to the removal of the heat of reaction. The presence of steam, carbon dioxide or the like in the feed mixture not only permits easy control of the reaction temperature but also improves reaction yield. Since carbon dioxide is the major by-product in the reaction effluent, it is practical to recycle the gas effluent after removal of citraconic anhydride and maleic anhydride. The amount of steam or recycle gas effluent present in the feed mixture is not critical, and can be selected from a wide range. The usual amount is from 0 to about 95 percent, preferably from about 10 to 80 percent, by volume.

A variety of feedstocks containing isoamylenes (that is, 3-methyl-1-butene, 2-methyl-1-butene or 2-methyl-2-butene) may be used. Either pure isoamylene or hydrocarbon feedstocks from, for example, gasoline fractions or other refinery streams containing isoamylene in admixture with other hydrocarbons (saturated or unsaturated), for example, isoamylene-isoprene, isoamylene-isopentane and combinations thereof, may be used. Isoprene, pure or in admixture with other hydrocarbons, can also be converted to citraconic anhydride with excellent yields when using the catalysts of the present invention. Based on current economics, isoprene is not a preferred commercial feedstock for the oxidation process; it is, however, within the scope of the present invention. The preferred feedstock is one consisting of or containing isoamylene.

The flow rate of the gaseous feed through the reactor may be varied within rather wide limits, but the preferred range is from about 4 to 84,000 grams of hydrocarbon per liter of catalyst per hour and more preferably from about 10 to 40,000 grams of hydrocarbon per liter of catalyst per hour. Residence, or contact, times of the gaseous feed will normally be less than about 5 seconds, more preferably from about 0.1 to 1.0 second. For commercial operations, a short residence time is generally desired, but times below about 0.1 second, while possible, are impractical. The residence time is the calculated dwell time in the reactor (empty reactor basis) at the reaction temperature:

$$\text{Residence Time} = \frac{\text{Weight of Catalyst (g)/Catalyst Bulk Density (g/cc)}}{\text{Gaseous Feed at Reaction Temperature (cc/sec)}}$$

The temperature of reaction may be varied within wide limits generally useful in known oxidation processes. Under usual operating conditions, in compliance with the preferred procedure of this invention, the reaction temperature may vary from about 300° to 650° C., preferably from about 370° to 570° C. and most preferredly from about 390° to 510° C. The pressure on the reactor is not generally critical, since the reaction may be conducted at atmospheric, superatmospheric or subatomspheric pressure, and conveniently will be about atmospheric pressure. In this connection, the temperature, pressure and residence requirements are interrelated and may be varied to produce optimum yield and selectivity. However, such adjustment follows the general principles already well known in the art with other catalyst systems and is no more critical here than with known vapor phase oxidations using other catalysts.

The anhydrides produced in the process of the present invention may be recovered from the gaseous reactor effluent by any of the methods well known in the art, such as conversion to the corresponding dibasic acids and separation of such acids.

In order to illustrate the invention more fully, attention is directed to the following examples. However, these examples are not intended to limit the invention.

EXAMPLE I

This example illustrates the preparation of antimony-molybdenum-oxygen catalysts which were used in the following examples.

Type A

The catalyst was prepared by refluxing 145.75 grams (0.5 mole) antimony trioxide powder and 23.03 grams (0.16 mole) molybdenum trioxide powder in 1 liter of water. After four hours refluxing, 42.4 grams of zirconium oxide* was added as a carrier. The mixture was then evaporated to a thick paste and dried in an oven overnight at between 100° and 120° C. at ambient pressure. The resulting product (184 grams) was ground and sieved to a particle size of 8–12 mesh (U.S. sieves).

* Norton Chemical Company BZ 5264; 94% zirconium oxide, 3.5% calcium oxide, less than 1% hafium oxide and less than 3% other oxides.

Type B

Type A catalyst was pulverized and slurried in water to form a paste. Twenty grams of an additional catalyst support, stainless steel shavings 1/16 × ⅝ × 1/100 inch thick, was heated to 200° C. and dipped into the paste. The coated shavings were dried in an oven at about 200° C. and the coating process was repeated until the shavings were completely covered with catalyst. The preparation was then left overnight in an atmospheric oven at 120° C. The amount of active catalyst applied on the shavings was about 10.5 grams.

EXAMPLE II

This example illustrates the effect of temperature, contact time and support variations on yield of citraconic anhydride. All the runs were carried out in fixed bed glass reactors having internal volumes of about 4 to 10 cc and with a feed containing 0.8 to 1.0 volume percent hydrocarbon in air. The results are as follows:

Table A

| Run No. | Feedstock | Catalyst | Reaction Temp. °C | Contact Time (Seconds) | Dibasic Acids, Wt. % Citraconic | Maleic | Molar Selectivity |
|---|---|---|---|---|---|---|---|
| 1 | Isoamylene | Type A | 465 | 0.34 | 47.0 | 6.8 | 6.1 |
| 2 | Isoamylene | Type A | 454 | 0.34 | 46.4 | 5.8 | 7.1 |
| 3 | Isoamylene | Type A | 440 | 0.34 | 43.2 | 3.5 | 11.1 |
| 4 | Isoamylene | Type A | 396 | 1.00 | 12.4 | 1.3 | 8.5 |
| 5 | Isoamylene | Type A | 396 | 1.76 | 29.7 | 5.1 | 5.2 |
| 6 | Isoamylene | Type A | 460 | 0.60 | 43.5 | 8.0 | 4.9 |
| 7 | Isoamylene | Type A | 460 | 1.47 | 40.9 | 10.4 | 3.5 |
| 8 | Isoamylene | Type B | 460 | 0.60 | 45.3 | 13.0 | 3.1 |
| 9 | Isoamylene | Type B | 460 | 1.47 | 46.1 | 12.1 | 3.4 |
| 10 | Isoprene | Type A | 446 | 0.34 | 71.3 | 10.4 | 6.1 |
| 11 | Isoprene | Type A | 476 | 0.16 | 65.6 | 8.4 | 7.0 |

EXAMPLE III

This example illustrates the effect of feed gas composition on yield. All runs were carried out using Type A catalyst. The reaction itself was carried out in glass reactors as in Example II.

Table B

| Run No. | Feed Gas, Mole Percent Isoamylene | $O_2$ | $N_2$ | $CO_2$ | Reaction Temp. °C | Contact Time (Seconds) | Yield To Citraconic Acid Wt. % |
|---|---|---|---|---|---|---|---|
| 1 | 0.8 | 78.4 | 20.8 | — | 448 | 0.27 | 52.6 |
| 2 | 0.8 | 39.0 | 60.2 | — | 458 | 0.36 | 49.0 |
| 3 | 0.9 | 31.2 | 67.9 | — | 450 | 0.41 | 49.0 |
| 4 | 0.8 | 20.6 | 78.6 | — | 460 | 0.33 | 46.8 |
| 5 | 1.0 | 15.0 | 84.0 | — | 470 | 0.51 | 42.9 |
| 6 | 1.0 | 10.0 | 89.0 | — | 460 | 0.43 | 32.9 |
| 7 | 0.8 | 85.2 | — | 14.0 | 455 | 0.28 | 60.4 |
| 8 | 0.8 | 85.2 | — | 14.0 | 446 | 0.42 | 58.3 |
| 9 | 0.8 | 85.2 | — | 14.0 | 426 | 0.98 | 58.7 |
| 10 | 0.8 | 40.0 | — | 59.2 | 455 | 0.38 | 54.0 |
| 11 | 0.8 | 40.0 | — | 59.2 | 436 | 0.73 | 54.4 |

The above table shows that citraconic acid yields in excess of 60 weight percent per pass can be obtained by using the catalyst of this invention. Since the conversion of isoamylene in the oxidation reaction is usually 90–95% completion, the actual yields to citraconic acid, if calculated on the amount of isoamylene consumed, are about 5–10% higher.

EXAMPLE IV

This example illustrates the outstanding life of the catalyst used in the invention for the oxidation of hydrocarbons. In the following runs 0.8 volume percent isoamylene in a mixture gas containing 40 volume percent oxygen and 59.2 volume percent $CO_2$ was fed to a reactor similar to that used in Example II at a salt bath temperature of 426° C. and at a contact time of about 0.4 second. Type A catalyst as described in Example I was used. The results obtained are shown in Table C.

Table C

| Catalyst Life (Days) | Weight Percent Yield Citraconic Acid |
|---|---|
| 0 | 53.8 |
| 1 | 54.6 |
| 2 | 54.4 |
| 27 | 55.7 |
| 31 | 55.2 |

The above shows that over the test period there was no catalyst deactivation.

EXAMPLE V

This example shows that other catalysts which contain either antimony or molybdenum do not share the unique ability of the catalyst of the present invention for the oxidation of isoamylene to citraconic anhydride. Furthermore, this example shows that catalysts which have been said to be active for oxidizing butene or butane to maleic anhydride are relatively ineffective in oxidizing isoamylene to citraconic anhydride.

All the catalysts except the V/P/Zn and V/P/W systems listed in Tables D-I and D-II were prepared in the manner described in Example I (Type A) with the exception that the listed elements were used. The V/P/Zn and V/P/W catalysts were prepared according to the procedures exemplified in DOS 2,261,907 and U.S. Pat. No. 3,478,063, respectively.

the maximum citraconic yield. The range of citraconic acid yield obtained over the range scanned is shown in Table D-II below.

Table D-II

| Run Series No. | Catalyst | Range of Yield at Condition Scanned, Citraconic Acid Weight Percent |
|---|---|---|
| 1 | Mo | 0–28.2 |
| 2 | Mo/Bi | Trace–7.0 |
| 3 | Mo/V | 8.3–22.3 |
| 4 | Mo/Sn | 0–7.0 |
| 5 | Mo/W/Sn | 0.33–7.0 |
| 6 | Mo/As | 5.6–21.0 |
| 7 | Sb | 0 |
| 8 | Sb/Bi | 0 |
| 9 | V/P/Zn | 0.55–1.8 |
| 10 | V/P/W | Trace–1.0 |
| 11 | V/P/Zn | 0–9.6 |

The above tables clearly show that the listed catalysts are markedly inferior to the catalyst of this invention. Also, it is clear that catalysts which have been previously said to be active in oxidizing butene or butane to maleic anhydride are relatively ineffective in oxidizing the corresponding hydrocarbons containing methyl group to citraconic anhydride. Instead, the predominant product is maleic anhydride.

EXAMPLE VI

This example illustrates the effect of additional elements previously taught to be catalytically active when added to the antimony-molybdenum-oxygen catalyst of the present invention. The example was carried out in a manner similar to that of Example V. The catalysts were prepared as in Example I (Type A) and the individual catalysts were scanned for optimum citraconic Table D-1

Feed: Isoamylene 1 % in Air (Runs 1–10)
Isopentane 1 % in Air (Run 11)

| | | Range Scanned | | Maximum Yield, Wt. % | |
|---|---|---|---|---|---|
| Run No. | Catalyst | Atomic Ratio | Reaction Temp. ° C | Contact Time (sec) | Citraconic | Maleic at Maximum Citraconic |
| 1 | Mo | — | 430–447 | 1.6–4.6 | 28.2 | 6.0 |
| 2 | Mo/Bi | 1/.11 | 419–450 | 0.76–3.0 | 7.0 | — |
| 3 | Mo/V | 1/.8 | 350–430 | 0.10–0.54 | 22.3 | 8.0 |
| 4 | Mo/Sn | 1/.67 | 350–440 | 0.50–3.5 | 7.0 | — |
| 5 | Mo/W/Sn | 1/.02/.08 | 313–464 | 0.11/0.88 | 7.0 | 6.6 |
| 6 | Mo/As | 1/1 | 417–463 | 0.46–1.38 | 21.0 | 7.3 |
| 7 | Sb | — | 426–467 | 0.20–6.3 | 0 | — |
| 8 | Sb/Bi | 1/1.5 | 400–450 | 0.50–3.0 | 0 | — |
| 9 | V/P/Zn | 1/1.15/.19 | 300–480 | 0.10–1.5 | 1.8 | 33.0 |
| 10 | V/P/W | 1/3.22/.13 | 455–459 | 0.5–1.1 | 1.0 | 16.0 |
| 11 | V/P/Zn | 1/1.15/.19 | 468 | 0.29 | 9.6 | 34.8 |

In the above table, temperature and contact time were varied over the range stated in an effort to maximize citraconic production. The maximum citraconic acid yield obtainable within the range scanned is reported as is the corresponding yield of maleic acid at yield over the ranges reported.

The results are shown in Table E.

Table E

Feed: Isoamylene 0.88 % in Air

| | | | Condition Range Scanned | | Maximum Yield, Wt. % | |
|---|---|---|---|---|---|---|
| Run No. | Catalyst | Atomic Ratio | Reaction Temp. ° C. | Contact Time (sec) | Citraconic Acid | Maleic at Maximum Citraconic Acid |
| 1 | Sb/Mo/Fe | 1/.16/1 | 378–450 | 0.2–1.0 | 35.6 | Trace |
| 2 | Sb/Mo/Fe | 1/.16/.16 | 384–453 | 0.2–1.0 | 36.9 | 4.3 |
| 3 | Sb/Mo/V | 1/.16/1 | 410–510 | 0.2–1.0 | 0 | 0 |
| 4 | Sb/Mo/V | 1/.16/.16 | 380–456 | 0.1–1.1 | 18.6 | 6.6 |
| 5 | Sb/Mo/V/P | 1/1.5/1/.125 | 380–464 | 0.2–0.5 | 27.8 | 5.0 |
| 6 | Sb/Mo | 1/.16 | 380–465 | 0.3–1.0 | 47.0 | 6.8 |

This example shows that the inclusion of additional active elements such as iron or vanadium in the antimony-molybdenum-oxygen catalyst of the present invention reduces the yield of citraconic obtainable.

EXAMPLE VII

This example illustrates various atomic ratios of antimony to molybdenum useful according to the present invention. All of the catalysts were prepared in the same manner as described in Example I (Type A) except that different weights of antimony and molybdenum were used. The results are summarized in Table F.

Table F

Feed: Isoamylene 0.8 Mole % in Air

| Run No. | Atomic Ratio Sb/Mo | Condition Range Scanned | | Maximum Yield Citraconic | | |
|---|---|---|---|---|---|---|
| | | Temp. °C | Contact Time (Seconds) | Temp. °C | Contact Time (Seconds) | Weight Percent Citraconic Acid |
| 1 | 1/0.16 | 360–470 | .33–1.83 | 461 | 0.33 | 46.8 |
| 2 | 1/0.25 | 426–490 | .13–1.06 | 433 | 1.06 | 40.7 |
| 3 | 1/1.50 | 360–440 | .58–1.57 | 395 | 1.57 | 42.3 |
| 4 | 1/9.50 | 360–440 | .41–1.37 | 391 | 1.28 | 40.1 |

This example demonstrates that the high yields obtainable when using the present invention are applicable over a wide range of atomic ratios. As in Examples V and VI, the temperatures and contact times were varied over the range stated to obtain maximum citraconic yield.

EXAMPLE VIII

This example illustrates the effect of various catalyst supports in catalysts according to the present invention. The catalysts were made in accord with Example I (Type A) except for the use of a different carrier. The results are shown in Table G.

Table G

Isoamylene 1 % in Air

| Run No. | Sb/Mo | Catalyst Support | Weight Ratio Catalyst/Support | Reaction Temp. °C | Contact Time (Seconds) | Yield Citraconic Acid, Wt. % |
|---|---|---|---|---|---|---|
| 1 | 1/.16 | ZrO$_2$ | 80/20 | 460 | 0.60 | 43.5 |
| 2 | 1/.16 | Alundum | 50/50 | 460 | 0.61 | 41.5 |

What we claim is:

1. In the process for the preparation of citraconic anhydride by catalytic vapor phase oxidation of a hydrocarbon selected from the group consisting of isoamylene, isoprene or mixtures thereof at a temperature of from about 300 to about 650° C., in the presence of a gas containing molecular oxygen, and at a contact time of from about 0.1 to about 5.0 seconds, the improvement which comprises carrying out said oxidation in the presence of a catalyst consisting essentially of antimony, molybdenum and oxygen, the antimony being present in an amount of from about 0.01 to 100 atoms for each atom of molybdenum.

2. The process according to claim 1 wherein said hydrocarbon is isoamylene.

3. The process according to claim 2 wherein the concentration of said isoamylene in the feed mixture to the oxidation is from about 0.1 to about 20 mole percent.

4. The process according to claim 1 wherein said catalyst contains from about 0.05 to 15 atoms of antimony per atom of molybdenum.

5. The process according to claim 1 wherein said catalyst is deposited on a support.

6. The process according to claim 1 wherein said oxidation is carried out at a temperature of from about 390° C. to about 510° C. and the contact time is from about 0.1 to about 1.0 second.

7. The process according to claim 1 wherein said hydrocarbon is isoamylene contained in a feed having from about 0.1 to about 20 mole percent isoamylene, the temperature is from about 390° C. to about 510° C., the contact time is from about 0.1 to about 1.0 second and said catalyst contains from about 0.05 to 15 atoms of antimony per atom of molybdenum.

8. The process according to claim 7 wherein said catalyst is supported on a carrier.

* * * * *